United States Patent
Dove et al.

(10) Patent No.: US 10,188,511 B2
(45) Date of Patent: *Jan. 29, 2019

(54) BIOPROSTHETIC TISSUE WITH REDUCED CALCIFICATION

(71) Applicant: Edwards Lifesciences Corporation, Irvine, CA (US)

(72) Inventors: Jeffrey S. Dove, Santa Ana, CA (US); Darin P. Dobler, Aliso Viejo, CA (US); James A. Davidson, San Juan Capistrano, CA (US); Gregory A. Wright, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,123

(22) Filed: Apr. 25, 2016

(65) Prior Publication Data
US 2016/0235528 A1    Aug. 18, 2016

Related U.S. Application Data

(60) Division of application No. 14/707,970, filed on May 8, 2015, now Pat. No. 9,320,830, which is a (Continued)

(51) Int. Cl.
*A61F 2/24*    (2006.01)
*A61L 27/36*   (2006.01)
(Continued)

(52) U.S. Cl.
CPC .......... *A61F 2/2415* (2013.01); *A61F 2/0095* (2013.01); *A61F 2/24* (2013.01);
(Continued)

(58) Field of Classification Search
None
See application file for complete search history.

(56) References Cited

U.S. PATENT DOCUMENTS 2,393,580 A    1/1946  Weiskopf
2,484,813 A   10/1949  Bower
(Continued)

FOREIGN PATENT DOCUMENTS

EP    0169259 A1    1/1986
EP    2394673 A1   12/2011
(Continued)

OTHER PUBLICATIONS

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

(Continued)

*Primary Examiner* — Robert A Wax
*Assistant Examiner* — Melissa S Mercier
(74) *Attorney, Agent, or Firm* — Sheppard Mullin; Michelle Kim

(57) ABSTRACT

A treatment for bioprosthetic tissue used in implants or for assembled bioprosthetic heart valves to reduce in vivo calcification. The method includes applying a calcification mitigant such as a capping agent or an antioxidant to the tissue to specifically inhibit oxidation in tissue. Also, the method can be used to inhibit oxidation in dehydrated tissue. The capping agent suppresses the formation of binding sites in the tissue that are exposed or generated by the oxidation and otherwise would, upon implant, attract calcium, phosphate, immunogenic factors, or other precursors to calcification. In one method, tissue leaflets in assembled biopros- (Continued)

thetic heart valves are pretreated with an aldehyde capping agent prior to dehydration and sterilization.

17 Claims, 8 Drawing Sheets

Related U.S. Application Data continuation of application No. 14/139,367, filed on Dec. 23, 2013, now Pat. No. 9,029,418, which is a continuation of application No. 13/745,496, filed on Jan. 18, 2013, now Pat. No. 8,748,490, which is a continuation of application No. 12/338,872, filed on Dec. 18, 2008, now Pat. No. 8,357,387.

(60) Provisional application No. 61/016,263, filed on Dec. 21, 2007.

(51) Int. Cl.
 *A61L 27/50* (2006.01)
 *A61F 2/00* (2006.01)

(52) U.S. Cl.
 CPC .......... *A61F 2/2412* (2013.01); *A61F 2/2418* (2013.01); *A61L 27/3604* (2013.01); *A61L 27/3625* (2013.01); *A61L 27/3629* (2013.01); *A61L 27/3687* (2013.01); *A61L 27/3691* (2013.01); *A61L 27/507* (2013.01); *A61L 2400/02* (2013.01); *A61L 2430/20* (2013.01)

(56) References Cited

U.S. PATENT DOCUMENTS

| | | | |
|---|---|---|---|
| 2,567,929 A | 9/1951 | Fessenden | |
| 4,067,091 A | 1/1978 | Backman | |
| 4,120,649 A | 10/1978 | Schechter | |
| 4,120,991 A | 10/1978 | Ornstein et al. | |
| 4,197,658 A | 4/1980 | Fraser | |
| 4,207,689 A | 6/1980 | Romera-Sierra et al. | |
| 4,244,992 A | 1/1981 | von Hagens | |
| 4,294,753 A | 10/1981 | Urist | |
| 4,323,358 A | 4/1982 | Lentz et al. | |
| 4,328,256 A | 5/1982 | Romero-Sierra et al. | |
| 4,347,671 A | 9/1982 | Dias et al. | |
| 4,350,492 A | 9/1982 | Wright et al. | |
| 4,372,743 A | 2/1983 | Lane | |
| 4,378,224 A | 3/1983 | Nimni et al. | |
| 4,402,697 A | 9/1983 | Pollock et al. | |
| 4,405,327 A | 9/1983 | Pollock | |
| 4,481,009 A | 11/1984 | Nashef | |
| 4,553,974 A | 11/1985 | Dewanjee | |
| 4,599,084 A | 7/1986 | Nashef | |
| 4,624,822 A | 11/1986 | Arru et al. | |
| 4,647,283 A | 3/1987 | Carpentier et al. | |
| 4,648,881 A | 3/1987 | Carpentier et al. | |
| 4,655,773 A | 4/1987 | Grassi | |
| 4,676,070 A | 6/1987 | Linner | |
| 4,729,139 A | 3/1988 | Nashef | |
| 4,753,652 A | 6/1988 | Langer et al. | |
| 4,755,593 A * | 7/1988 | Lauren ................ | A61L 27/3604 128/DIG. 8 |
| 4,770,665 A | 9/1988 | Nashef | |
| 4,776,853 A | 10/1988 | Klement et al. | |
| 4,786,287 A | 11/1988 | Nashef et al. | |
| 4,831,065 A | 5/1989 | Pietsch et al. | |
| 4,838,888 A | 6/1989 | Nashef | |
| 4,865,871 A | 9/1989 | Livesey et al. | |
| 4,885,005 A | 12/1989 | Nashef et al. | |
| 4,891,319 A | 1/1990 | Roser | |
| 4,958,008 A | 9/1990 | Petite et al. | |
| 4,975,526 A | 12/1990 | Kuberasampath et al. | |
| 4,976,733 A | 12/1990 | Girardot | |
| 4,994,030 A | 2/1991 | Glowczewskie, Jr. et al. | |
| 4,994,237 A | 2/1991 | Login et al. | |
| 4,996,054 A | 2/1991 | Pietsch et al. | |
| 5,002,566 A | 3/1991 | Carpentier et al. | |
| 5,011,913 A | 4/1991 | Benedict et al. | |
| 5,024,830 A | 6/1991 | Linner | |
| 5,044,165 A | 9/1991 | Linner et al. | |
| 5,051,401 A | 9/1991 | Sikes | |
| 5,068,100 A | 11/1991 | McClanahan | |
| 5,080,670 A | 1/1992 | Imamura et al. | |
| 5,094,661 A | 3/1992 | Levy et al. | |
| 5,104,405 A | 4/1992 | Nimni | |
| 5,108,923 A | 4/1992 | Benedict et al. | |
| 5,116,564 A | 5/1992 | Jansen et al. | |
| 5,147,514 A | 9/1992 | Mechanic | |
| 5,149,621 A | 9/1992 | McNally et al. | |
| 5,149,653 A | 9/1992 | Roser | |
| 5,154,007 A | 10/1992 | Piunno et al. | |
| 5,200,399 A | 4/1993 | Wettlaufer et al. | |
| 5,215,541 A | 6/1993 | Nashef et al. | |
| 5,279,612 A | 1/1994 | Eberhardt | |
| 5,290,558 A | 3/1994 | O'Leary et al. | |
| 5,296,583 A | 3/1994 | Levy | |
| 5,329,846 A | 7/1994 | Bonutti | |
| 5,332,475 A | 7/1994 | Mechanic | |
| 5,336,616 A | 8/1994 | Livesey et al. | |
| 5,368,608 A | 11/1994 | Levy et al. | |
| 5,397,353 A | 3/1995 | Oliver et al. | |
| 5,424,047 A | 6/1995 | Zwingenberger et al. | |
| 5,436,291 A | 7/1995 | Levy et al. | |
| 5,437,287 A | 8/1995 | Phillips et al. | |
| 5,447,536 A | 9/1995 | Girardot et al. | |
| 5,447,724 A | 9/1995 | Helmus et al. | |
| 5,460,962 A | 10/1995 | Kemp | |
| 5,476,516 A | 12/1995 | Seifter et al. | |
| 5,507,813 A | 4/1996 | Dowd et al. | |
| 5,509,932 A | 4/1996 | Keogh et al. | |
| 5,556,379 A | 9/1996 | Wolfinbarger | |
| 5,558,875 A | 9/1996 | Wang | |
| 5,595,571 A | 1/1997 | Jaffe et al. | |
| 5,613,982 A | 3/1997 | Goldstein | |
| 5,632,778 A | 5/1997 | Goldstein | |
| 5,645,587 A | 7/1997 | Chanda et al. | |
| 5,674,298 A | 10/1997 | Levy et al. | |
| 5,679,112 A | 10/1997 | Levy et al. | |
| 5,695,729 A | 12/1997 | Chow et al. | |
| 5,695,820 A | 12/1997 | Davis et al. | |
| 5,697,972 A | 12/1997 | Kim et al. | |
| 5,713,953 A | 2/1998 | Vallana et al. | |
| 5,720,777 A | 2/1998 | Jaffe et al. | |
| 5,720,894 A | 2/1998 | Neev et al. | |
| 5,733,339 A | 3/1998 | Girardot et al. | |
| 5,746,775 A | 5/1998 | Levy et al. | |
| 5,762,600 A | 6/1998 | Bruchman et al. | |
| 5,766,520 A | 6/1998 | Bronshtein | |
| 5,769,780 A | 6/1998 | Hata et al. | |
| 5,776,182 A | 7/1998 | Bruchman et al. | |
| 5,782,914 A | 7/1998 | Schankereli | |
| 5,782,915 A | 7/1998 | Stone | |
| 5,782,931 A | 7/1998 | Yang et al. | |
| 5,843,180 A | 12/1998 | Jaffe et al. | |
| 5,843,181 A | 12/1998 | Jaffe et al. | |
| 5,843,182 A | 12/1998 | Goldstein | |
| 5,855,620 A | 1/1999 | Bishopric et al. | |
| 5,856,102 A | 1/1999 | Bierke-Nelson et al. | |
| 5,856,172 A | 1/1999 | Greenwood et al. | |
| 5,862,806 A | 1/1999 | Cheung | |
| 5,865,849 A | 2/1999 | Stone | |
| 5,873,812 A | 2/1999 | Ciana et al. | |
| 5,879,383 A | 3/1999 | Bruchman et al. | |
| 5,882,850 A | 3/1999 | Khor et al. | |
| 5,899,936 A | 5/1999 | Goldstein | |
| 5,902,338 A | 5/1999 | Stone | |
| 5,904,718 A | 5/1999 | Jefferies | |
| 5,911,951 A | 6/1999 | Girardot et al. | |
| 5,913,900 A | 6/1999 | Stone | |
| 5,919,472 A | 7/1999 | Trescony et al. | |
| 5,921,980 A | 7/1999 | Kim | |
| 5,922,027 A | 7/1999 | Stone | |
| 5,931,969 A | 8/1999 | Carpentier et al. | |

(56) References Cited

U.S. PATENT DOCUMENTS

| | | |
|---|---|---|
| 5,935,168 A | 8/1999 | Yang et al. |
| 5,945,319 A | 8/1999 | Keogh |
| 5,977,153 A | 11/1999 | Camiener |
| 5,987,720 A | 11/1999 | Yamamoto |
| 5,993,844 A | 11/1999 | Abraham et al. |
| 6,008,292 A | 12/1999 | Lee et al. |
| 6,017,741 A | 1/2000 | Keogh |
| 6,024,735 A | 2/2000 | Wolfinbarger, Jr. |
| 6,063,120 A | 5/2000 | Stone |
| 6,066,160 A | 5/2000 | Colvin et al. |
| 6,093,204 A | 7/2000 | Stone |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,258,320 B1 | 7/2001 | Persing et al. |
| 6,267,786 B1 | 7/2001 | Stone |
| 6,277,555 B1 | 8/2001 | Duran et al. |
| 6,287,338 B1 | 9/2001 | Samowski et al. |
| 6,290,991 B1 | 9/2001 | Roser et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,322,994 B1 | 11/2001 | Reid |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,372,228 B1 | 4/2002 | Gregory |
| 6,375,680 B1 | 4/2002 | Carlyle |
| 6,376,244 B1 | 4/2002 | Atala |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle |
| 6,471,723 B1 | 10/2002 | Ashworth et al. |
| 6,479,079 B1 | 11/2002 | Pathak et al. |
| 6,482,199 B1 | 11/2002 | Neev |
| 6,506,339 B1 | 1/2003 | Girardot et al. |
| 6,509,145 B1 | 1/2003 | Torrianni |
| 6,527,979 B2 | 3/2003 | Constantz |
| 6,531,310 B1 | 3/2003 | Mirsch, II et al. |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,586,006 B2 | 7/2003 | Roser et al. |
| 6,586,573 B1 | 7/2003 | Besman et al. |
| 6,589,591 B1 | 7/2003 | Mansouri et al. |
| 6,605,667 B1 | 8/2003 | Badejo et al. |
| 6,613,278 B1 | 9/2003 | Mills et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,682,559 B2 | 1/2004 | Myers et al. |
| 6,685,940 B2 | 2/2004 | Andya et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,828,310 B2 | 12/2004 | Barresi et al. |
| 6,872,226 B2 | 3/2005 | Cali et al. |
| 6,878,168 B2 | 4/2005 | Carpentier et al. |
| 6,893,666 B2 | 5/2005 | Spievack |
| 6,908,591 B2 | 6/2005 | MacPhee et al. |
| 6,911,043 B2 | 6/2005 | Myers et al. |
| 6,919,172 B2 | 7/2005 | DePablo et al. |
| 6,933,326 B1 | 8/2005 | Griffey et al. |
| 7,008,763 B2 | 3/2006 | Cheung |
| 7,029,434 B2 | 4/2006 | Carpentier et al. |
| 7,037,333 B2 | 5/2006 | Myers et al. |
| 7,063,726 B2 | 6/2006 | Crouch et al. |
| 7,087,723 B2 | 8/2006 | Besman et al. |
| 7,141,064 B2 | 11/2006 | Scott et al. |
| 7,143,769 B2 | 12/2006 | Stoltz et al. |
| 7,214,344 B2 | 5/2007 | Carpentier et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,358,284 B2 | 4/2008 | Griffey et al. |
| 7,367,969 B2 | 5/2008 | Stoltz et al. |
| RE40,570 E | 11/2008 | Carpentier et al. |
| 7,498,565 B2 | 3/2009 | Silberberg et al. |
| 7,579,381 B2 * | 8/2009 | Dove .................. A61L 27/3604 424/422 |
| 7,594,974 B2 | 9/2009 | Cali et al. |
| 7,648,676 B2 | 1/2010 | Mills et al. |
| 7,682,304 B2 | 3/2010 | Heyninck-Jantz et al. |
| 7,914,569 B2 | 3/2011 | Nguyen et al. |
| 7,919,112 B2 | 4/2011 | Pathak et al. |
| 7,972,376 B1 * | 7/2011 | Dove .................. A61L 27/3604 435/1.1 |
| 8,007,992 B2 * | 8/2011 | Tian .................... A61L 27/3604 435/1.1 |
| 8,043,450 B2 | 10/2011 | Cali et al. |
| 8,075,615 B2 | 12/2011 | Eberhardt et al. |
| 8,105,375 B2 | 1/2012 | Navia et al. |
| 8,136,218 B2 | 3/2012 | Millwee et al. |
| 8,308,797 B2 | 11/2012 | Paniagua et al. |
| 8,357,387 B2 * | 1/2013 | Dove .................. A61L 27/3604 424/423 |
| 8,361,144 B2 | 1/2013 | Fish et al. |
| 8,377,143 B2 | 2/2013 | Hamby et al. |
| 8,475,827 B2 | 7/2013 | Hamby et al. |
| 8,748,490 B2 * | 6/2014 | Dove .................. A61L 27/3604 424/423 |
| 9,029,418 B2 * | 5/2015 | Dove .................. A61L 27/3604 424/423 |
| 9,066,785 B2 * | 6/2015 | Tran ...................... A61F 2/0095 |
| 9,320,830 B2 * | 4/2016 | Dove .................. A61L 27/3604 |
| 9,320,930 B2 * | 4/2016 | Abels .................... A62C 37/08 |
| 2001/0000804 A1 | 5/2001 | Goldstein et al. |
| 2001/0020191 A1 | 9/2001 | Williams et al. |
| 2001/0025196 A1 | 9/2001 | Chinn et al. |
| 2001/0027344 A1 | 10/2001 | Bonutti |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0091441 A1 | 7/2002 | Guzik |
| 2002/0111532 A1 | 8/2002 | Pathak et al. |
| 2003/0035843 A1 | 2/2003 | Livesey et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0212454 A1 | 11/2003 | Scott et al. |
| 2004/0030381 A1 | 2/2004 | Shu |
| 2004/0086543 A1 | 5/2004 | Keogh et al. |
| 2004/0158320 A1 | 8/2004 | Simionescu et al. |
| 2004/0193259 A1 | 9/2004 | Gabbay |

(56) References Cited

U.S. PATENT DOCUMENTS

| | | |
|---|---|---|
| 2005/0010773 A1 | 1/2005 | Lapstun et al. |
| 2005/0119736 A1 | 6/2005 | Zilla et al. |
| 2005/0136510 A1 | 6/2005 | Hendriks et al. |
| 2005/0211680 A1 | 9/2005 | Li et al. |
| 2006/0084957 A1 | 4/2006 | Delfyett et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0177426 A1 | 8/2006 | Gibson et al. |
| 2006/0193885 A1 | 8/2006 | Leonard Neethling et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2007/0292459 A1 | 12/2007 | Cooper et al. |
| 2008/0302372 A1 | 12/2008 | Davidson et al. |
| 2008/0319166 A1 | 12/2008 | Shen |
| 2009/0041729 A1 | 2/2009 | Wolfinbarger, Jr. et al. |
| 2009/0130162 A2 | 5/2009 | Pathak et al. |
| 2009/0137999 A1 | 5/2009 | Silberberg et al. |
| 2009/0188900 A1 | 7/2009 | Cali et al. |
| 2009/0326524 A1 | 12/2009 | Cali et al. |
| 2010/0036484 A1 | 2/2010 | Hariton et al. |
| 2011/0092966 A1 | 4/2011 | Guo et al. |
| 2011/0177150 A1 | 7/2011 | Pathak et al. |
| 2011/0214398 A1 | 9/2011 | Liburd et al. |
| 2011/0238167 A1 | 9/2011 | Dove et al. |
| 2011/0295363 A1 | 12/2011 | Girard et al. |
| 2011/0300625 A1 | 12/2011 | Paniagua et al. |
| 2011/0306124 A1 | 12/2011 | Strasly et al. |
| 2011/0311493 A1 | 12/2011 | Dove et al. |
| 2012/0035720 A1 | 2/2012 | Cali et al. |
| 2012/0059487 A1 | 3/2012 | Cunanan et al. |
| 2012/0067855 A1 | 3/2012 | Guo et al. |
| 2012/0078356 A1 | 3/2012 | Fish et al. |
| 2012/0095551 A1 | 4/2012 | Navia et al. |
| 2012/0123557 A1 | 5/2012 | Carpentier et al. |
| 2012/0185038 A1 | 7/2012 | Fish et al. |
| 2012/0328905 A1 | 12/2012 | Guo et al. |
| 2013/0122583 A1 | 5/2013 | Neethling |
| 2013/0238088 A1 | 9/2013 | Navia et al. |

FOREIGN PATENT DOCUMENTS

| | | |
|---|---|---|
| WO | 84/01894 A1 | 5/1984 |
| WO | 95/11047 A1 | 4/1995 |
| WO | 95/022361 A1 | 8/1995 |
| WO | 95/034332 A1 | 12/1995 |
| WO | 96/013227 A1 | 5/1996 |
| WO | 98007452 A1 | 2/1998 |
| WO | 98043556 A1 | 10/1998 |
| WO | 00/032252 A1 | 6/2000 |
| WO | 03/037227 A2 | 5/2003 |
| WO | 2004/082536 A1 | 9/2004 |
| WO | 2006/026325 A2 | 3/2006 |
| WO | 2006/099334 A2 | 9/2006 |
| WO | 2013009581 A2 | 1/2013 |

OTHER PUBLICATIONS

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as a Ligament Substitute," Journal of Biomedical Materials Research, vol. 21, No. 12, pp. 1383-1394, 1987, University of Arizona health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves after Glycerol Dehydration, Ethylene Oxide Steilization, and Rehydration," Innovations, vol. 6, No. 1, Jan./ Feb. 2011.

Grabenwoger, M., et al., "Decreased Tissue Reaction to Bioprosthetic Heart Valve Material after L-glutamic acid Treatment. A Morphological Study," J. Biomed Mater. Res. Sep. 1992; 26(9): 1231-40.

Grant, R.A., et al., The Effects of Irradiation With High Energy Electrons on the Structure and Reactivity of Native and Cross-Linked Collagen Fibres, 1970, pp. 387-405, J. Cell Sci 7.

Hauschka, P., et al., Direct Identification of the Calcium-Binding Amino Acid .gamma.-Carboxyglutamate, in Mineralized Tissue, Oct. 1975, pp. 3295-3929, Proc. Nat. Acad. Sci, vol. 72, No. 10.

Jayakrishnan, A., et al., "Glutaraldehyde as a Fixative in Bioprostheses and Drug Delivery Matrices," Biomaterial, vol. 17, Issue 5, 1996, pp. 471-484.

Khora, Eugene, "Methods for the Treatment of Collagenous Tissues for Biopropstheses," Biomaterials, vol. 18, Issue. 2, Jan. 1997, pp. 95-105.

Liao, K., et al., "Mechanical Stress: An Independent Determinant of Early Bioprosthetic Calcification in Humans," Annals of Thoracic Surgery 2008;86: 491-495.

Nieethling, W., et al., "Enhanced Biostability and Biocompatibility of Decellularized Bovine Pericardium, Crosslinked with an Ultra-Low Concentration Monomeric Aldehyde and Treated with ADAPT®," J. Heart Valve Dis. 2008; 17: 456-464.

Ohan, M.P., et al., Glucose Stabilizes Collagen Sterilized With Gamma Irradiation, 2003, pp. 1188-1195, Wiley Periodicals, Inc., J Biomed Mater Res 67A.

Olde Damink, L.H.H., et al., Influence of Ethylene Oxide Gas Treatment on the in Vitro Degradation Behavior of Dermal Sheep Collagen, 1995, Journal of Biomedical Materials Research, vol. 29, 149-155, John Wiley & Sons, Inc.

PCT/US2008/013879 International Search Report Dated Mar. 11, 2009.

R Parker, et al. Storage of Heart Valve Allografts in Glycerol With Subsequent Antibiotic Sterilisation, Thorax, 1978, 538-645, vol. 33:5, British Thoracic Society, London, UK.

Saegeman, V., et al, "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterial, vol. 21, pp. 2215-2231, 2000.

Trantina-Yates, A.E., et al., "Detoxification of Top Enhanced, Diamine-Extended Glutaraldehyde Fixation Significantly Reduces Bioprosthetic Root Calcification in the Sheep Model," J. Heart Valve Dis. Jan. 2003; 12(1): 93-100.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

* cited by examiner

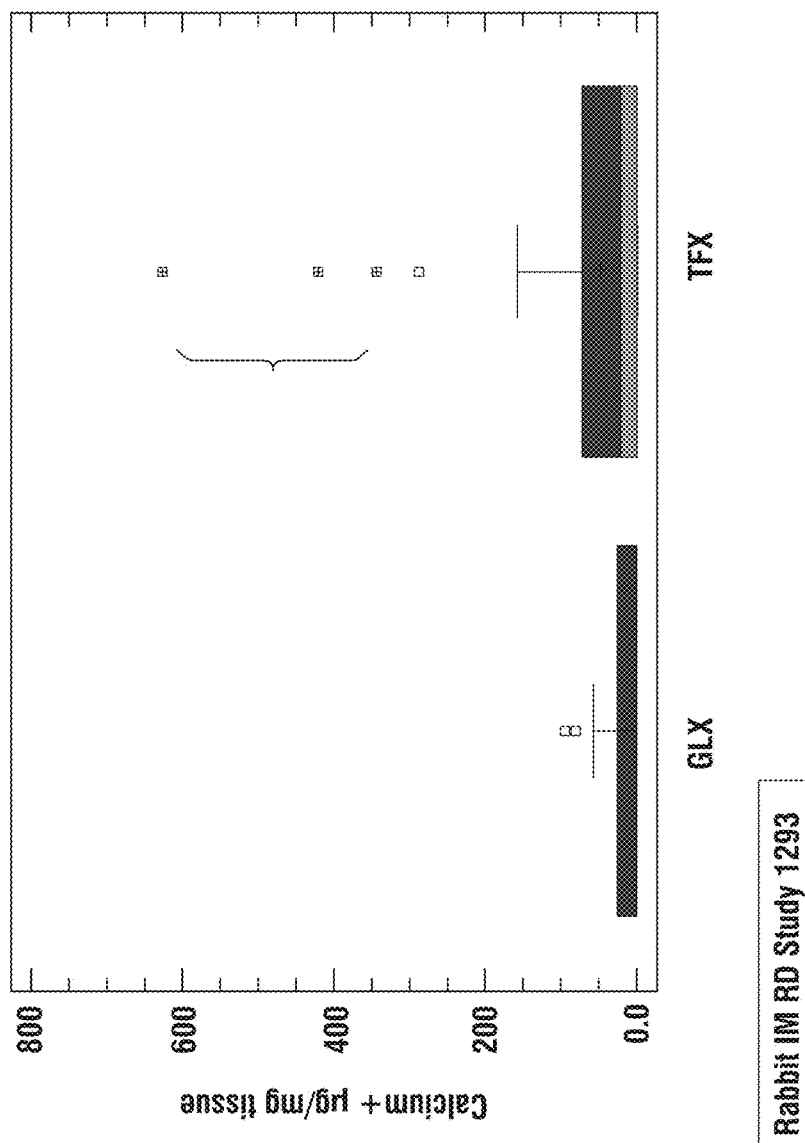

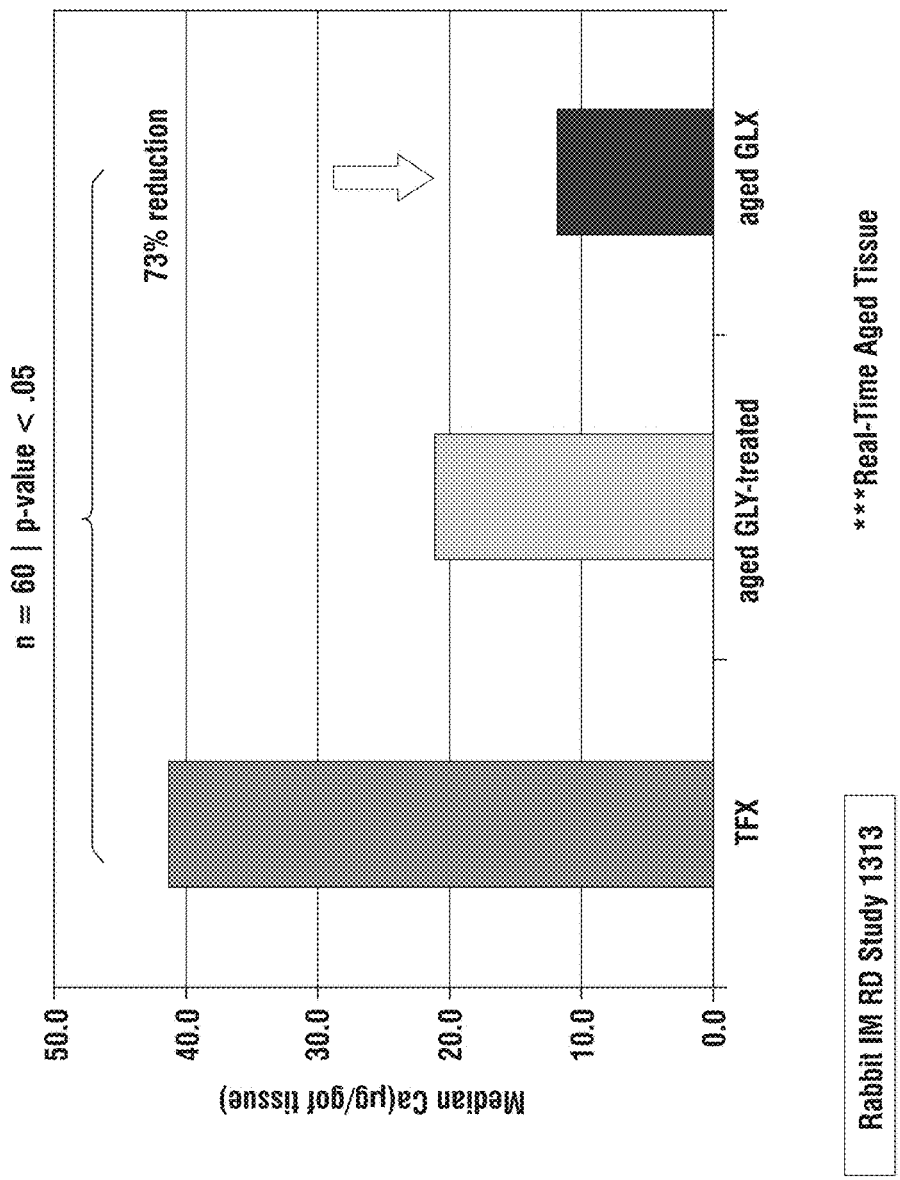

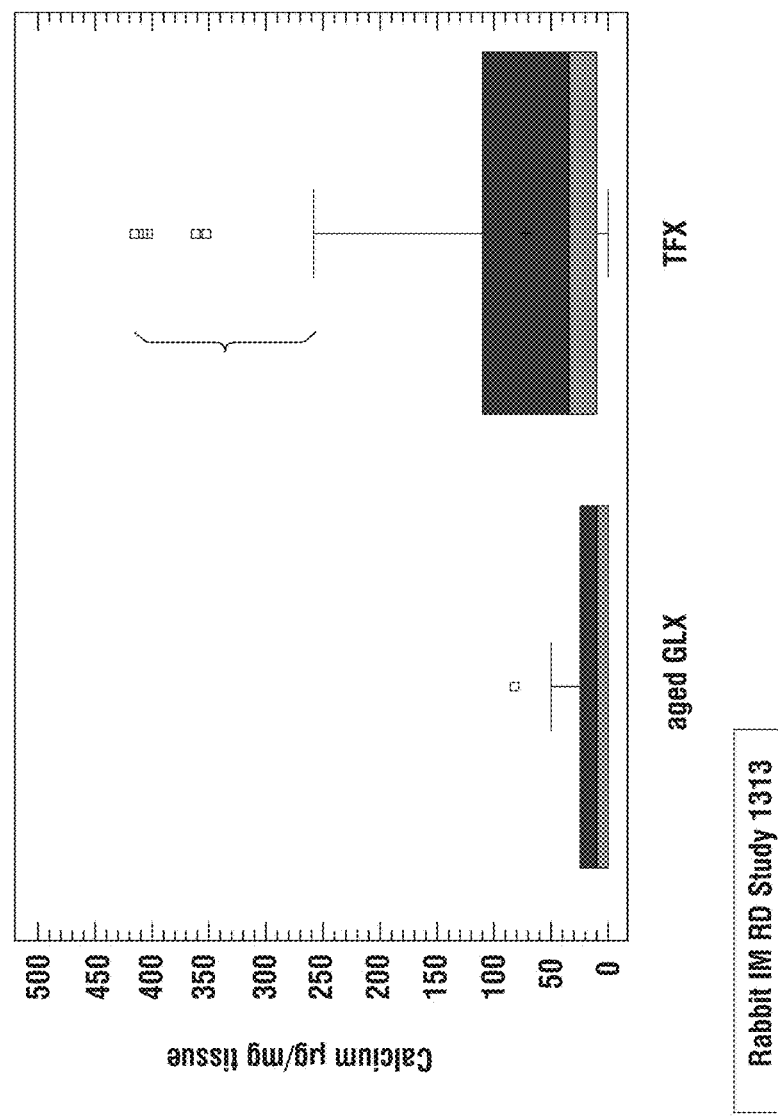

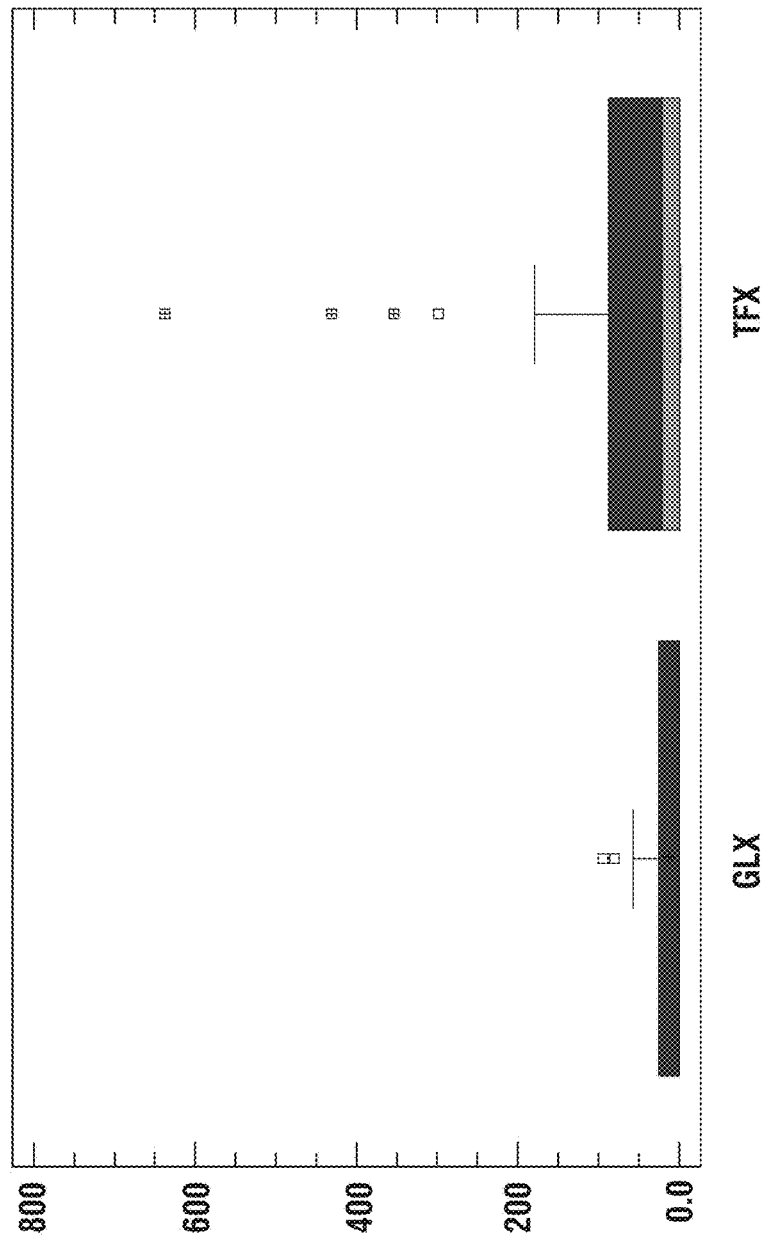

BIOPROSTHETIC TISSUE WITH REDUCED CALCIFICATION

CROSS-REFERENCE TO RELATED APPLICATIONS

This application is a divisional of U.S. patent application Ser. No. 14/707,970, filed May 8, 2015, now U.S. Pat. No. 9,320,830, which is a continuation of U.S. patent application Ser. No. 14/139,367, filed Dec. 23, 2013, now U.S. Pat. No. 9,029,418, which is a continuation of U.S. patent application Ser. No. 13/745,496, filed Jan. 18, 2013, now U.S. Pat. No. 8,748,490, which is a continuation of U.S. patent application Ser. No. 12/338,872 filed Dec. 18, 2008, now U.S. Pat. No. 8,357,387, which claims the benefit of U.S. Patent Application No. 61/016,263, filed Dec. 21, 2007, the entire disclosures of which are incorporated by reference herein.

FIELD OF THE INVENTION

The present invention relates generally to methods for treating bioprosthetic tissue, materials, and devices to reduce post-implantation calcification, and reducing post-implantation calcification, in particular for bioprosthetic tissue used in heart valves.

BACKGROUND OF THE INVENTION

Heart valve replacement may be indicated when there is a narrowing of the native heart valve, commonly referred to as stenosis, or when the native valve leaks or regurgitates, such as when the leaflets are calcified. In one therapeutic solution, the native valve may be excised and replaced with either a biologic or a mechanical valve. Certain medical conditions may require grafting or suturing a tissue patch to repair physiological abnormalities. These include, but are not limited to hernia repair, vascular wounds, congenital heart defect repair and reconstruction, and bladder wall repair.

Tissue-type or "bioprosthetic" valves have flexible tissue leaflets supported by a base structure that project into the flow stream and function much like those of a natural human heart valve by coapting against each other to ensure one-way blood flow. In tissue-type valves, a whole xenograft valve (e.g., porcine) or a plurality of xenograft leaflets (e.g., bovine or equine pericardium) typically provide fluid occluding surfaces. Synthetic tissue leaflets have also been proposed. One or more flexible leaflets mount within a peripheral support structure, for example as seen in the CARPENTIER-EDWARDS Porcine Heart Valve and PERIMOUNT Pericardial Heart Valve available from Edwards Lifesciences of Irvine, Calif.

Implantable biological tissues can be formed of human tissues preserved by freezing (i.e., cryopreservation) the homograft tissues, or of animal tissues preserved by chemically fixing (i.e., tanning) the xenograft tissues. The type of biological tissues used as bioprostheses include cardiac valves, blood vessels, skin, dura mater, pericardium, small intestinal submucosa ("SIS tissue"), ligaments and tendons. These biological tissues typically contain connective tissue proteins (i.e., collagen and elastin) that act as the supportive framework of the tissue. The pliability or rigidity of each biological tissue is largely determined by the relative amounts of collagen and elastin present within the tissue and/or by the physical structure and configuration of its connective tissue framework. Collagen is the most abundant connective tissue protein present in most tissues. Each collagen molecule is made up of three (3) polypeptide chains intertwined in a coiled helical configuration.

The techniques used for chemical fixation of biological tissues typically involve exposing the biological tissue to one or more chemical fixatives (i.e., tanning agents) which form cross-links between the polypeptide chains within a given collagen molecule (i.e., intramolecular cross-linkages), or between adjacent collagen molecules (i.e., intermolecular cross-linkages). Examples of chemical fixative agents that have been used to cross-link collagenous tissues include: formaldehyde, glutaraldehyde, dialdehyde starch, hexamethylene diisocyanate and certain polyepoxy compounds.

One problem associated with the implantation of many bioprosthetic materials is that the connective tissue proteins (i.e., collagen and elastin) within them can become calcified following implantation in the body. Such calcification can result in undesirable stiffening or degradation of the bioprosthesis. This damage to the collagenous tissue leads to valve failure.

Of the various chemical fixatives available, glutaraldehyde (also referred to as simply "glut") has been the most widely used since the discovery of its anti-immunological and anti-degenerative effects by Dr. Alain Carpentier in 1968. See Carpentier, A., *J. Thorac. Cardiovascular Surgery*, 58: 467-69 (1969). In addition, glutaraldehyde is one of the most common sterilization agents. Glutaraldehyde is therefore used as the preferred fixative and sterilant for many commercially available bioprosthetic products, such as in the bioprosthetic heart valves available from Edwards Lifesciences of Irvine, Cali. Glutaraldehyde creates potential calcium binding sites within the tissue that can lead to calcification in vivo, such as residual aldehydes, acids, Schiff bases, etc. These groups can contribute to calcification unless mitigated via capping. Mitigating such calcification is particularly important during storage, especially when the tissue is not being stored in aqueous solution.

Various techniques have been proposed for mitigating the in vivo calcification of glutaraldehyde-fixed bioprostheses or for otherwise improving the glutaraldehyde fixation process. Among these are methods described in U.S. Pat. No. 4,729,139 (Nashef); U.S. Pat. No. 4,885,005 (Nashef et al.); U.S. Pat. No. 4,648,881 (Carpentier et al.); U.S. Pat. No. 5,002,566 (Carpentier); EP 103947 (Pollock et al.), U.S. Pat. No. 5,476,516 (Seifter et al.), and U.S. Pat. No. 5,215,541 (Nashef et al.). The techniques in U.S. Pat. No. 5,862,806 (Cheung) include dehydration using an organic solution (i.e. ethanol, but no glycerol) of glutaraldehyde-treated tissues, prior to the application of a chemical reducing agent such as sodium cyanoborohydride or sodium borohydride in an organic solvent. This process involves only the addition of a reducing agent without any capping agents, such as proteins, amines or amino acids. The calcification mitigation techniques disclosed in U.S. Pat. No. 6,471,723 and U.S. Pat. No. 4,786,287 involve the addition of a variety of amines to detoxify the aldehyde groups in glutaraldehyde-fixed tissue. These chemicals are not permanently attached to the tissue (e.g., by addition of a reducing agent), and so diffuse out of the tissue over time, which dramatically lowers the calcium mitigation efficacy of these treatments. The techniques in U.S. Pat. No. 5,476,516 involve the addition of polyols (e.g., glycerol) and alcohols to bioprosthetic tissues as a calcification mitigation treatment alone, but do not address any oxidation mitigation (i.e., capping) strategies. U.S. Pat. No. 6,509,145 and U.S. Pat. No. 7,078,163 address oxidation of bioprosthetic tissue for the purpose of calcification mitigation. U.S. Pat. No. 6,630,001 and U.S.

Pat. No. 6,277,555 discuss the use of glycerol preservation and lyophilization of tissue, but do not discuss chemical methods to prevent oxidation. U.S. Pat. No. 6,352,708 includes glycerol preservation of fresh, "non-fixed" tissue, and treatments with glycerol and heparin, but does not include combinations of chemical treatments to prevent oxidation or reduce calcification with a glycerol drying step.

Recently a new technique of calcium mitigation by elevated-temperature fixation of the tissue in glutaraldehyde was described in U.S. Pat. No. 6,561,970 (Carpentier et al.) and in combination with relative tissue/fluid movement in U.S. Pat. No. 5,931,969 (Carpentier et al.). Another technique, involving adjusting the pH of a glutaraldehyde fixation solution, is disclosed in U.S. Pat. No. 6,878,168 (Carpentier et al.) The Edwards Lifesciences XenoLogiX™ Tissue Treatment eliminates up to 98% of phospholipids in an attempt to reduce calcium binding sites. In the Carpentier-Edwards ThermaFix™ Advanced Heart Valve Tissue Process, also from Edwards Lifesciences, both thermal and chemical treatments are used to remove unstable glutaraldehyde molecules and thus reduce calcium binding sites, resulting in a marked reduction in calcium uptake versus glutaraldehyde-only controls.

Bioprosthetic valves are generally stored in glutaraldehyde or formaldehyde solution, and must be rinsed prior to implantation. Glutaraldehyde is widely used as a storage solution due to its sterilant properties but is known to contribute to calcification. Strategies to minimize glutaraldehyde content in the final product have been demonstrated to mitigate in vivo calcification. Studies have shown that storage solutions without gluaraldehyde reduce in vivo calcification compared to those with glutaraldehyde. (Mirzaie, et al. *Ann Thorac Cardiovasc Surg* 2007 13:102).

One such strategy to avoid glutaraldehyde as a storage solution is to dehydrate the bioprosthetic tissue in a glycerol/ethanol mixture, sterilize with ethylene oxide, and package the final product "dry". This process circumvents the potential toxicity and calcification effects of glutaraldehyde as a sterilant and storage solution. There have been several methods proposed to use glycerine, alcohols, and combinations thereof as post-glut processing methods so that the resulting tissue is in a "dry" state rather than a wet state with excess glut. These approaches avoid the use of aqueous liquid aldehyde, or liquid sterilant as storage solutions for tissue and devices. Glycerol-based methods can be used for such storage as described in the following examples. The storage of heart valve tissue in glycerol was described by Parker et al. (*Thorax* 1978 33:638), but does not include any calcification mitigation techniques and does not describe any advantages. Also, U.S. Pat. No. 6,534,004 (Chen et al.) describes the storage of bioprosthetic tissue in polyhydric alcohols such as glycerol. However, neither of these addresses mitigating potential oxidation of the tissue.

In processes where the tissue is dehydrated in an ethanol/glycerol solution, the tissue may be sterilized by ethylene oxide, gamma irradiation, or electron beam irradiation. Ethylene oxide sterilization requires exposing the tissue to increased temperatures and water vapor which will generate oxidative damage in the tissue (Olde Damink, L H. et al. *J Biomed Mater Res* 1995 29:149). Gamma irradiation is known to generate significant reactive oxygen species in collagenous substrates which causes backbone scission and breakage of collagen fibrils (Ohan, M P et al. *J Biomed Mater Res A* 2003 67:1188). This damage will lead to decreased mechanical and biochemical functionality in the tissue. Electron beam irradiation will also cleave the collagen backbone and lead to deterioration of the tissue structure and reactivity (Grant, R A et al. *J Cell Sci* 1970 7:387). Damage from oxidation during sterilization and/or storage will contribute to valve deterioration and structural failure. U.S. Pat. No. 6,605,667 discusses the addition of various antioxidant stabilizers to polymerizable adhesives, but does not address damage mitigation to bioprosthetic tissue by ionizing radiation or oxidation during storage.

Although these glycerol-based methods are useful as alternatives to storage in aqueous, liquid-type solutions, they do not address the fact that the post-process functional groups (i.e. aldehydes) can oxidize over time and thus increase the potential for calcification. The present invention describes a capping method such that oxidation and other changes are dramatically reduced with storage time. The prior art does not address the changes within dehydrated bioprosthetic tissue during storage that occur as a result of in vitro oxidation by air or in vivo oxidation. The high aldehyde content in glutaraldehyde-fixed tissue is highly susceptible to oxidation, which results in calcification and tissue failure. Thus, the present invention teaches an improved tissue treatment method for implantable tissue devices.

The present invention addresses certain detrimental changes within dehydrated tissue that can occur as a result of oxidation either from sterilization, atmospheric exposure during storage and handling, or from in vivo oxidation. Storage of bioprosthetic tissue in glutaraldehyde provides some antioxidant effect and helps to prevent oxidation of the aldehyde functions in the tissue that are likely to contribute to increased calcification. In processes where the tissue is dehydrated and stored in air, the tissue is not protected from oxidation and will lead to biochemical damage from reactive oxygen species. The resulting oxidative biomarkers, such as carboxylic acids, are likely to promote calcium binding and proceed to failure of the bioprosthesis due to calcification. The permanent capping of the aldehyde groups in the tissue (reductive amination) will prevent significant oxidation of the tissue and lead to longer service lifetimes of the material. The present invention involves the chemical capping of aldehydes (and other species) or otherwise neutralizing of the tissue to prevent oxidation in dehydrated tissue.

The invention also describes the addition of chemicals (e.g. antioxidants) to the dehydration solution (ethanol/glycerol) to prevent oxidation of the tissue during sterilization (ethylene oxide, gamma irradiation, electron beam irradiation, etc.) and storage. Dehydrated bioprosthetic tissue is particularly susceptible to oxidation during sterilization and storage. The prior art does not discuss the chemical prevention of this damage for this type of bioprosthetic material.

SUMMARY OF THE INVENTION

One object of the invention is to provide a method of mitigating calcification in bioprosthetic implant tissue, comprising: a) treating bioprosthetic implant tissue with a capping agent that reacts with functional groups on said tissue, and b) dehydrating the capped tissue with a non-aqueous solution.

Another object is to provide calcification-resistant tissue, comprising: a) bioprosthetic implant tissue that has been treated with a capping agent which reacts with functional groups on said tissue, and b) dehydrated with a non-aqueous solution.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

FIG. 5 is a chart that indicates the reduction in calcification variability by capping, reduction and drying (GLX process);

FIG. 6 is a chart showing the decrease in calcification by capping, reduction and drying (GLX process) after 80 days of real time shelf life;

FIG. 7 is a box and whisker plot of 35 Day Rabbit Intramuscular Study.

FIG. 8 is a box and whisker plot of 35 Day Rabbit Intramuscular Study, Short Term Shelf Life and Calcification.

DESCRIPTION OF THE PREFERRED EMBODIMENTS

Figure 1:
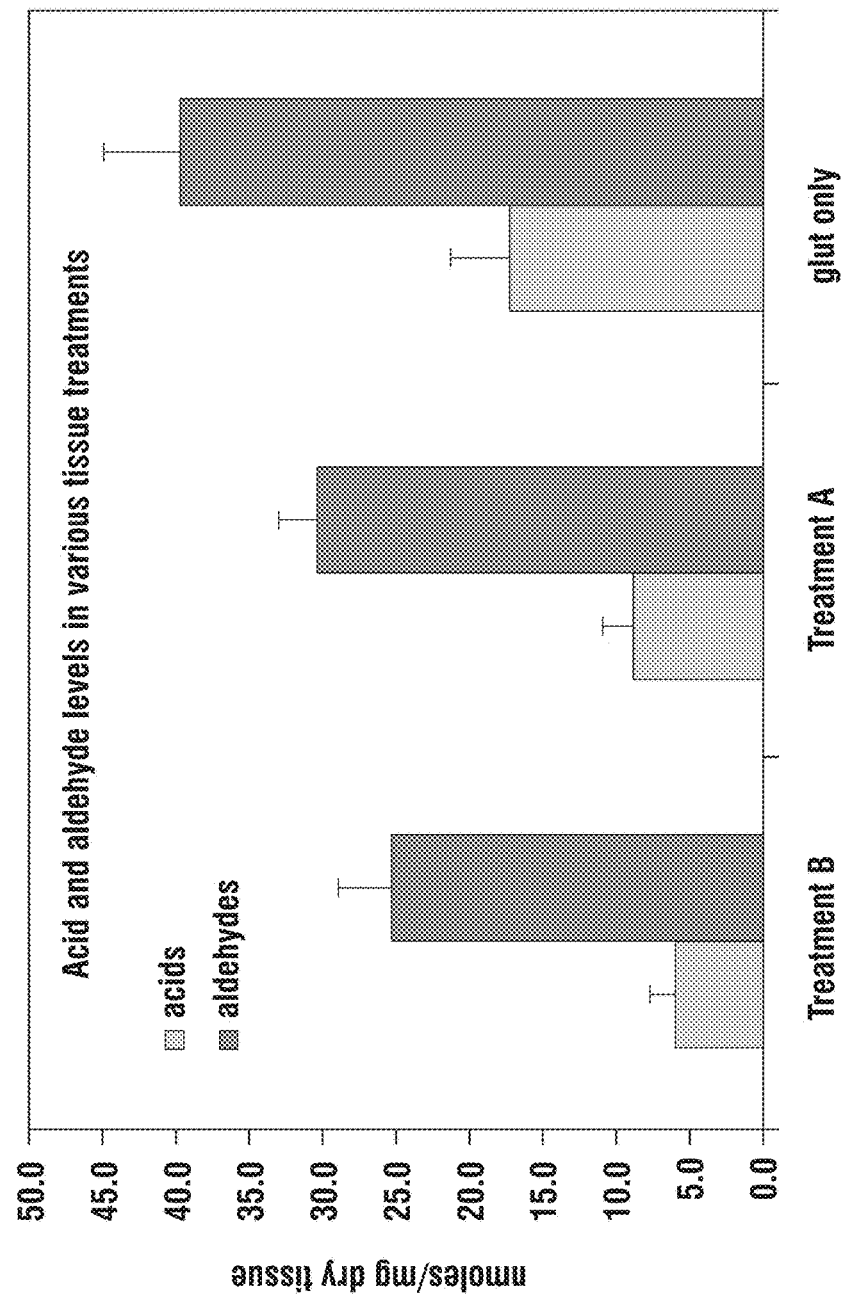
FIG. 1 is a graph showing the aldehyde and acid content in bovine pericardial tissue after several different chemical treatments.

The present invention provides an improved bioprosthetic tissue treatment process that greatly reduces the potential for calcification after implantation by blocking free aldehyde groups prior to a dehydration step and/or the addition of chemical agents to prevent oxidative damage during sterilization. "Bioprosthetic tissue" includes, without limitation, bovine pericardium and porcine tissue which are commonly used in bioprosthetic heart valves, and blood vessels, skin, dura mater, pericardium, small intestinal submucosa ("SIS tissue"), tissue heart valves, ligaments and tendons. "Implants" in the present application refers not only to heart valves, including transcatheter heart valves, but also to vascular prostheses and grafts, tissue grafts, bone grafts, and orbital implant wraps, among others.

A "bioprosthetic heart valve" refers to a fully assembled prosthetic valve made at least partly from bioprosthetic tissue. Some whole porcine valves are used in so-called "stentless" bioprosthetic valves in which there is very little if any synthetic material added for support or anchoring purposes. A "stented" bioprosthetic valve typically has some kind of synthetic (e.g., polymer or metallic) support for the leaflets, which may be the leaflets of a whole porcine xenograft or separate bovine pericardial leaflets. Heart valves contemplated herein include surgical heart valves, transapical heart valves, transfemoral heart valves and other types of heart valves.

Prior art tissue treatments address crosslinking, microbes, and other aspects of the tissue in a "static" setting, and typically involve immersion of the tissue in glutaraldehyde, Tween (polyoxyethylene 20 sorbitan monooleate), ethanol, formaldehyde, and other agents to mitigate post-implant calcification. Some prior art processes include the addition of various chemicals to reduce the toxicity of the crosslinked tissue or mitigate calcification via the use of metal ions (i.e., $Al^{3+}$ or $Fe^{3+}$ see U.S. Pat. No. 5,746,775, Levy) or bulk blocking agents (i.e., 2-amino oleic acid—see U.S. Pat. No. 4,976,733, Giradot). But each of these methods is only applied to initially processed tissue, not to dehydrated tissue or tissue devices to prevent oxidative damage. The prior art processes are limited to the addition of chemical or biological agents to crosslinked tissue that are temporarily attached to the tissue, or they are limited to reduction or oxidation of the tissue alone without any addition of "capping agents" (e.g., U.S. Pat. No. 5,862,806, Cheung).

Unlike the various prior art tissue processes, where the goal is to fix (i.e. crosslink, etc.) the tissue, this invention describes an additional process whereby acids and other potential binding sites formed from the prior art fixation processes are "capped." It also involves "capping" the binding sites and potential binding sites that are generated from oxidation of fixed tissue. Tissue treatment with glutaraldehyde, Tween (polyoxyethylene 20 sorbitan monooleate), ethanol, formaldehyde, and other agents can provide useful fixation of the tissue. However, it will also generate binding sites capable of interacting with or attracting calcium, phosphate, immunogenic factors, or other precursors to calcification. For example, there are many negatively charged carboxylic acid groups formed after glutaraldehyde fixation of the tissue, and these groups are capable of attracting calcium ions (due to their negative charge and electrostatic interactions with positively charged ions) leading to calcification of the tissue or adverse cellular interactions. Carboxylic acid groups like those in glutamic acid or gamma carboxy glutamic acid are known to bind calcium atoms (Hauschka et al. *PNAS* 1975 72:3925). Calcium binding proteins such as bone sialoprotein contain carboxylic acid-rich domains designed to attract and bind calcium, leading to hydroxyapatite formation (calcification). The overall level and location of acid groups in these proteins determines the ability of the protein to efficiently bind calcium and form hydroxyapatite. The term "acid potential" of the tissue refers to the level of these chemical functional groups within the fixed tissue which may eventually form acid groups or "binding sites" by oxidation, dehydration, hydration, or similar processes.

The inventors have discovered that such binding, causes significant post-implant damage in bioprosthetic materials, especially tissues used for heart valve leaflets. For example, the oxidative damage that occurs during storage and handling of dehydrated or "dry" tissue can create carboxylic acid groups that will bind calcium and lead to tissue failure. This progressive leaflet damage process can create new binding sites or potential binding sites that are precursors to calcification and immunogenic related pathways. The present invention describes a method to cap these newly formed binding sites prior to implantation of the tissue for tissue-based bioprosthetic into the body. The inventors have also discovered that bioprosthetic tissue exposed to oxidation from the atmosphere when not submersed in a glutaraldehyde solution or during sterilization is likely to contain more acid groups that contribute to calcification and inflammation. In dry storage, the dehydrated tissue is sterilized and stored "dry" without the protective effect of the glutaraldehyde solution. The ease of handling and storage of this new product is greatly facilitated due to the absence of the glutaraldehyde storage solution. This technology can be improved by treating such bioprosthetic tissue with a capping agent and/or adding a chemical protectant during the dehydration phase.

One chemical target within the invention is the permanent "capping" of the acid groups which dramatically reduces their ability to attract calcium, phosphate, immunogenic factors, or other groups. The term "capping" refers to the blocking, removal, or alteration of a functional group that would have an adverse effect on the bioprosthesis properties. For example, the addition of 1-ethyl-3-[3-dimethylaminopropyl]carbodiimide hydrochloride (EDC), N-hydroxysulfosuccinimide sulfo-NHS), and ethanolamine will effectively cap the acid groups with a non-reactive alcohol group.

In addition to acid binding sites, tissues treated with glutaraldehyde or other aldehyde-containing agents also yield tissue with many free aldehyde groups that cause increased toxicity, higher calcification, and involvement in immunogenic responses. These aldehyde groups can easily oxidize into carboxylic acid groups via air oxidation, in vivo blood oxidation, macrophage oxidation, and other similar oxidation pathways. Thus, an additional target of the invention includes the permanent capping of aldehyde groups, which are potential binding sites, in a way that would prevent or mitigate their ability to transform into acids or other groups and thus further mitigate the potential for calcification in the body (in vivo). In addition to acids and aldehydes there are other possible binding sites such as immunogenic and antigenic factors, capping which is included within the scope of this invention.

The present capping process includes chemical reduction of the tissue, which, when applied to the tissue in the presence of a capping agent, will permanently connect the capping agent to the target group. For example, the addition of ethanolamine to the tissue will cap the aldehyde groups, while the reducing agent (e.g., sodium borohydride) reduces any Schiff base created by reaction of the aldehyde with the amine group of ethanolamine. Thus an aldehyde is ultimately replaced by a hydroxyl group, which may be beneficial for tissue hydration, flexibility, and cell interactions. Of course, other capping agents can be used instead of ethanolamine and other reducing agents other than sodium borohydride and are known by those skilled in the art and which are included in the scope of this patent. Another preferred strategy is to oxidize the tissue aldehydes to acids, and then cap the acid groups. This may involve the addition of 1-ethyl-3-[3-dimethylaminopropyl]carbodiimide hydrochloride (EDC), N-hydroxysulfosuccinimide (sulfo-NHS), and ethanolamine. These new "capped" groups will reduce the attraction of calcium, phosphate, immunogenic factors, or other similar agents.

In one specific embodiment, the invention provides a method of treating bioprosthetic implant tissue to reduce in vivo calcification of comprising at least partially cross-linking bioprosthetic implant tissue, then treating the cross-linked tissue with an aldehyde (or acid) capping solution to mitigate calcification, and dehydrating the tissue in an ethanol/glycerol solution. The glycerol solution may include an antioxidant treatment and may contain a water-soluble wax. The tissue is then allowed to dry and then subjected to final sterilization (e.g., ethylene oxide, gamma irradiation, or electron beam irradiation). The following steps describe an implementation of this process in the manufacture of prosthetic heart valves.

Aldehyde Capping. After the valve leak and flow inspection, the valves are briefly rinsed in 20% ethane to remove any excess glutaraldehyde adhering to the tissue. This is thought to enhance the capping process by ensuring that the capping solution can attach to aldehydes on the tissue rather than free glutaraldehyde in solution. The valves are then exposed to a capping solution of ethanolamine and sodium borohydride, at room temperature under agitation for 4 hours. Valves are removed from the capping solution, and rinsed for a few minutes at room temperature with the same solution used in the final bioburden reduction process to remove excess capping solution.

Glycerol Treatment. After the valves have been processed through a standard final bioburden reduction step, they undergo the glycerol treatment in a solution of 75 wt % glycerol and 25 wt % ethanol. Valves are soaked in this solution for one hour at room temperature. During this time, most of the water molecules present in the pericardial tissue are replaced with glycerol. Valves are removed from the solution and placed in a clean hood to allow any excess solution to evaporate or drip off the valves.

EO Sterilization. The dehydrated valves are then ready for packaging. They are packaged in double sterile barrier packaging consisting of a rigid tray (PETG) with a Tyvek lid. The package is sealed in a cleanroom, and sterilized in 100% ethylene oxide.

The calcification mitigant preferably contains a capping agent selected from:
an amine,
an amino acid,
an amino sulfonate,
a hydrophilic multifunctional polymer,
a hydrophobic multifunctional polymer,
α-dicarbonyl,
a hydrazides,
a N,N-disuccinimidyl carbonate,
a carbodiimide,
2-chloro-1-methylpyridinium iodide (CMPI),
an antibiotic,
a cell recruiting agent,
a hemocompatibility agent,
an antiinflamatory agent,
an antiproliferative agent,
an immunogenic suppressing agent,
a reducing agent, and
a mono-, di- or polyepoxy alkane.

The chemical anti-oxidant is desirably selected from:
a water soluble antioxidant such as
ascorbic acid,
a fat soluble antioxidant such as
tocopherols,
a carbohydrate such as
fructose,
sucrose,
or mannitol
a hindered phenol such as
butylated hydroxytoluene (BHT),
a hindered amine light stabilizer (HALS) such as
p-phenylamine diamine,
trimethyl dihydrodquinoline,
or alkylated diphenyl amines
a phosphite/phosphonite such as
triphenyl phosphine,
and a thioester such as
a thiocinnamate The calcification mitigant (capping agent) and/or the chemical oxidation protectant is desirably delivered in one or a combination of the following selected solutions:
an aqueous solution such as an aqueous buffered solution, water, short chain alcohols, glycerol, or plasticizers,
an organic solvent, and
an organic buffered solution.

The tissue is preferably fully cross-linked prior to the capping process. In one embodiment, the tissue comprises precut heart valve leaflets mounted and treated in a suitable apparatus. Alternatively, the tissue may be bulk sheets of tissue treated in a suitable apparatus.

Examples of capping agents, provided in species and subspecies, are: amines,
   alkyl amines,
   amino alcohols,
   ethanolamine,
   amino acids,
   lysine,
   hydroxylysine,
   amino sulfonates,
   taurine,
   amino sulfates,
   dextran sulfate,
   chondroitin sulfate,
   hydrophilic multifunctional polymer,
   polyvinyl alcohol,
   polyethyleneimine,
   hydrophobic multifunctional polymer,
   α-dicarbonyls
   methylglyoxal
   3-deoxyglucosone
   glyoxal
   hydrazides
   adipic hydrazide
   N,N-disuccinimidyl carbonate
   carbodiimides
   1-ethyl-3-[3-dimethylaminopropyl]carbodiimide hydrochloride (EDC)
   N-cyclohexyl-N'-(2-morpholinoethyl)carbodiimide (CMC)
   1,3-dicyclohexyl carbodiimide (DCC)
   2-chloro-1-methylpyridinium iodide (CMPI)
   an antibiotic,
   a cell recruiting agent,
   a hemocompatibility agent,
   heparin,
   an anti-inflammatory agent,
   an antiproliferative agent,
   an immunogenic suppressing agent,
   a reducing agent,
   sodium cyanoborohydride,
   sodium borohydride,
   sodium bisulfite+acetylacetone,
   formic acid+formaldehyde, and
   mono-, di- or polyepoxy alkanes.

The effect of preferred capping agents is to not only block functional groups that will attract calcium, phosphate, immunogenic factors, or other similar agents, but to replace those groups with a superior biological functionality. The term "biological functionality" is defined as the effect of tissue components on the local biology of the implanted material. Improved biological functionality of a tissue treatment may include reduction in overall charge of the tissue, better hemocompatibility, increased tissue hydration, better cell interactions, better flexibility, etc. For example, capping aldehyde functions with ethanolamine blocks the aldehyde group from oxidizing into an acid and replaces it with a hydroxyl group, which may be beneficial for tissue hydration, flexibility, and cell interactions. The desired biological functionality of the capped tissue will determine the type of capping compounds employed.

The capping strategy is also designed to block the biological functionality of components of the tissue that may contribute to adverse cellular reactions. Some of these targets include, but are not limited to α-gal, MHC-1 associated proteins, HLA antigens and the like. The invention addresses the capping or blocking of proteins, carbohydrates, lipids, and other components of the tissue that may contribute to cellular reactions. For example, the α-gal carbohydrate may be blocked by treatment with 2-chloro-1-methylpyridinium iodide (CMPI) and other agents that neutralize the hydroxyl groups which are known by those skilled in the art. Another example includes MHC-1 associated proteins that may be capped or effectively neutralized by treatment with 1-ethyl-3-[3-dimethylaminopropyl]carbodiimide hydrochloride (EDC) and ethanolamine. Also included in the invention's capping process is the targeting of proteins, carbohydrates or lipids associated with cell and vessel remnants. For example, fibronectin may be capped or blocked by the addition of methylglyoxal to the tissue. This dicarbonyl is known to bind critical arginine functions within proteins and impairs the biological functionality of these proteins.

Another aspect of the invention includes the activation of capping technology upon sterilization. For example, the treatment of tissue with specific capping agents (e.g. glucose and ethanolamine or taurine) prior to gamma irradiation sterilization would produce activation of the capping agents upon irradiation. The capping agents added to the tissue would effectively cap targets within the tissue immediately, but sterilization (i.e. ethylene oxide, electron beam irradiation, or gamma irradiation) would generate new binding sites that would then be capped by the residual capping agents within the tissue. Gamma irradiation of collagen is known to cleave peptide bonds within the backbone and produce new functional groups that may have adverse effects on the tissue. These new functional groups are included in the targets or binding sites described herein and may be capped or blocked by the capping agents listed herein.

Immunogenic factors are defined as anything causing or involved in stimulating an immunogenic response. These include any chemical or biological agent capable of inducing an immune type response. For example, vessel and cell membrane components left in the tissue may cause some type of immunogenic or antigenic response from the body's natural immune system. The invention includes capping agents capable of masking, replacing, or blocking these immunogenic elements in the tissue either statically or dynamically. For example, a whole valve could be fixed, then capped with a non-immunogenic or more hemocompatible capping agent such as heparin prior to dehydration and sterilization. This is different from prior art processes that add heparin to fixed tissue without any dehydration of the valve or any consideration of the post-process oxidation conditions. The invention process can be supplemented with a decellularization process to reduce immunologic or antigenic binding sites and potential binding sites and is also within the scope of this invention.

To better understand the principles underlying the treatment techniques of the present invention, a number of graphs in (see the Figures) are presented based on actual testing. As mentioned above, the invention generally comprises treating tissue so that calcium or phosphate binding sites, or other such sites which could trigger calcification, are capped. The correlation between acid binding sites and tissue calcification can be seen in (FIG. 2 see also Hauschka et al. *PNAS* 1975 72:3925.) and it appears that acid templating directs mineralization in a variety of species. Thus, the amount of free acids and/or aldehydes in the tissue at the time of implantation correlates with the number of such binding sites and, therefore, increases the potential for calcification. The amount of free acids and aldehydes present in tissue can be measured by known methods, for example, a standard spectrophotometric assay.

FIG. 1 is a graph showing both the free aldehyde and free acid content in bovine pericardial tissue as measured by the aforementioned technique. It should be understood that all of the tests referred to herein involve glutaraldehyde-fixed bovine pericardial tissue. The tissues studied have all been chemically treated, one with glutaraldehyde only, and two others with tissue treatments that have been used by Edwards Lifesciences to prepare commercial bioprosthetic tissue for implant. However, other cross-linking and tissue processing methods can be used and are within the scope of this invention.

The aldehyde and acid content of the tissues is measured subsequent to the chemical treatments, and without any damage or stress imparted to the tissue. On the right side of the graph of FIG. 1, the tissue samples have been treated in glutaraldehyde only, in particular in a solution of 0.625% glutaraldehyde for a period of 14 days. A total of 10 samples were treated and subsequently tested. The measurements showed an average level of about 40 nanomoles of aldehydes and about 17 nanomoles of acids per milligram of dry weight of the tissue.

The middle of the graph of FIG. 1 shows the results from testing a total of 10 tissue samples subjected to Treatment A, which is commercially known as the XenoLogiX™ tissue treatment process from Edwards Lifesciences of Irvine, Calif. Treatment A involves first fixing with glutaraldehyde then treating twice with a sterilant including a cross-linking agent such as formaldehyde, a surfactant such as Tween-80 (Polyoxyethylene sorbitan monooleate), and a denaturant such as ethyl alcohol. Both the aldehyde and acid content of the tissue subjected to Treatment A were less than that of tissue treated with glutaraldehyde alone, with the aldehyde content decreasing by about 25% and the acid content by about 50%. This reduction has been attributed to the further reduction of phospholipids which are sources of acid binding sites as well as hemiacetal formation from alcohol and aldehyde groups.

The left side of FIG. 1 shows the results from testing a total of 10 samples subjected to Treatment B, which is commercially known as the Carpentier-Edwards Therma-Fix™ tissue treatment process from Edwards Lifesciences. Treatment B is essentially the same as Treatment A, with the addition of a heat treating step after fixing and prior to sterilizing. Both the aldehyde and acid content of the tissue subjected to Treatment B were less than that of tissue treated with glutaraldehyde alone, with the aldehyde content decreasing by about 33% and the acid content by more than 50%. In addition, Treatment B reduces both the aldehyde and acid content relative to Treatment A by between 10-20%.

Figure 2:
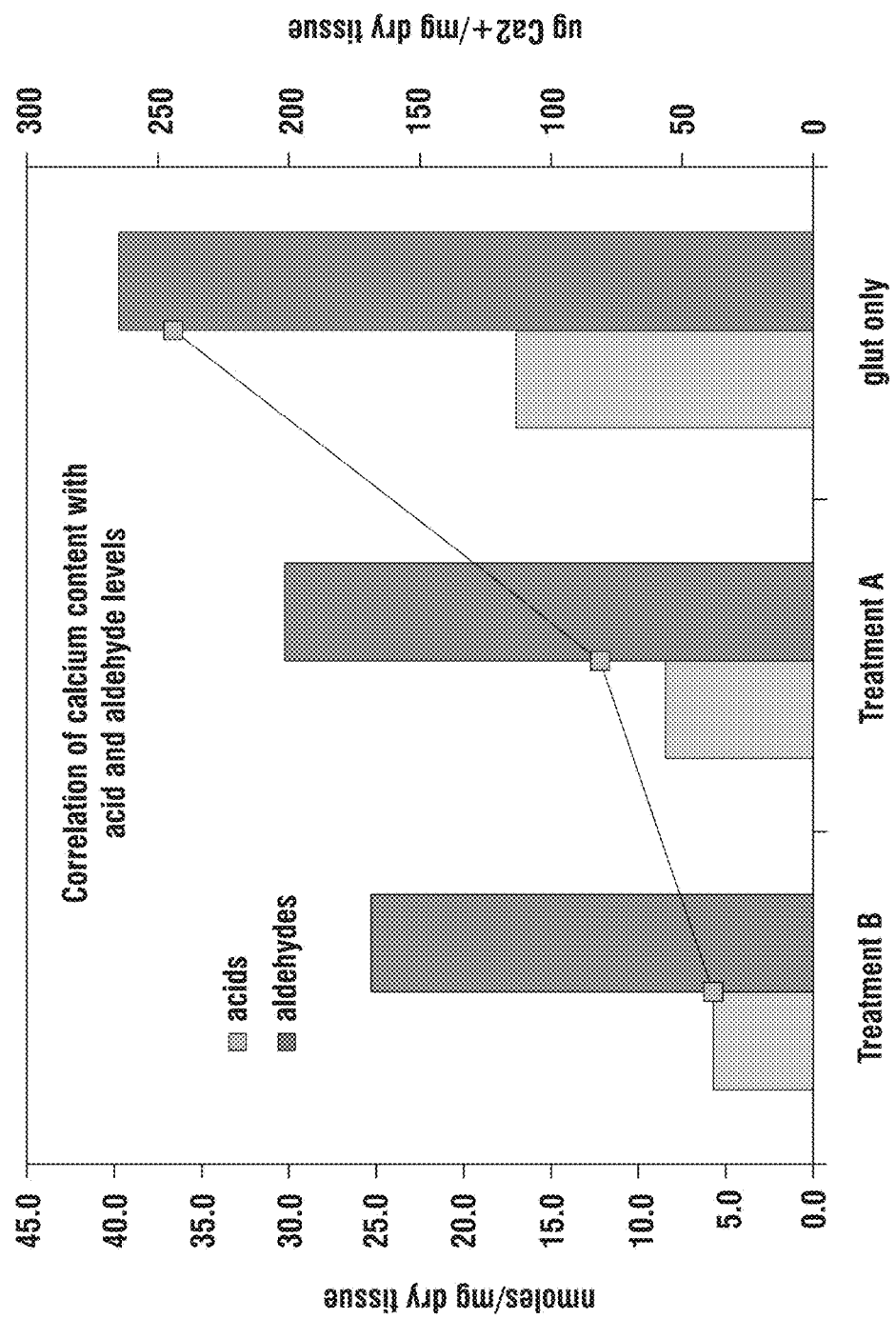
FIG. 2 is a graph correlating the calcium content of in vivo tissue with the corresponding acid and aldehyde content for tissue treated three different ways.

FIG. 2 is a graph that repeats the results of aldehyde/acid content measurements for the three tissue treatments shown in FIG. 1, and also superimposes measurements of calcium uptake from like tissue samples implanted subcutaneously in rabbits from a separate study. These acid levels are measured in the tissue prior to implant and are likely to increase in vivo. FIG. 2 reveals that the amount of calcium found in the implanted tissues correlates with the levels of aldehydes/acids from the three tissue treatments. That is, as the level of free aldehydes and free acids in the various tissue samples decreases, the amount of calcium absorbed upon implant also decreases. Again, it is understood that a number of factors contribute to calcium uptake, but the availability of certain calcium and phosphate binding sites, among others, is a prime indicator of future calcification. The graph of FIG. 2 therefore suggests that decreasing the levels of aldehydes/acids in the tissue will reduce the propensity for the tissue to calcify.

Figure 3:
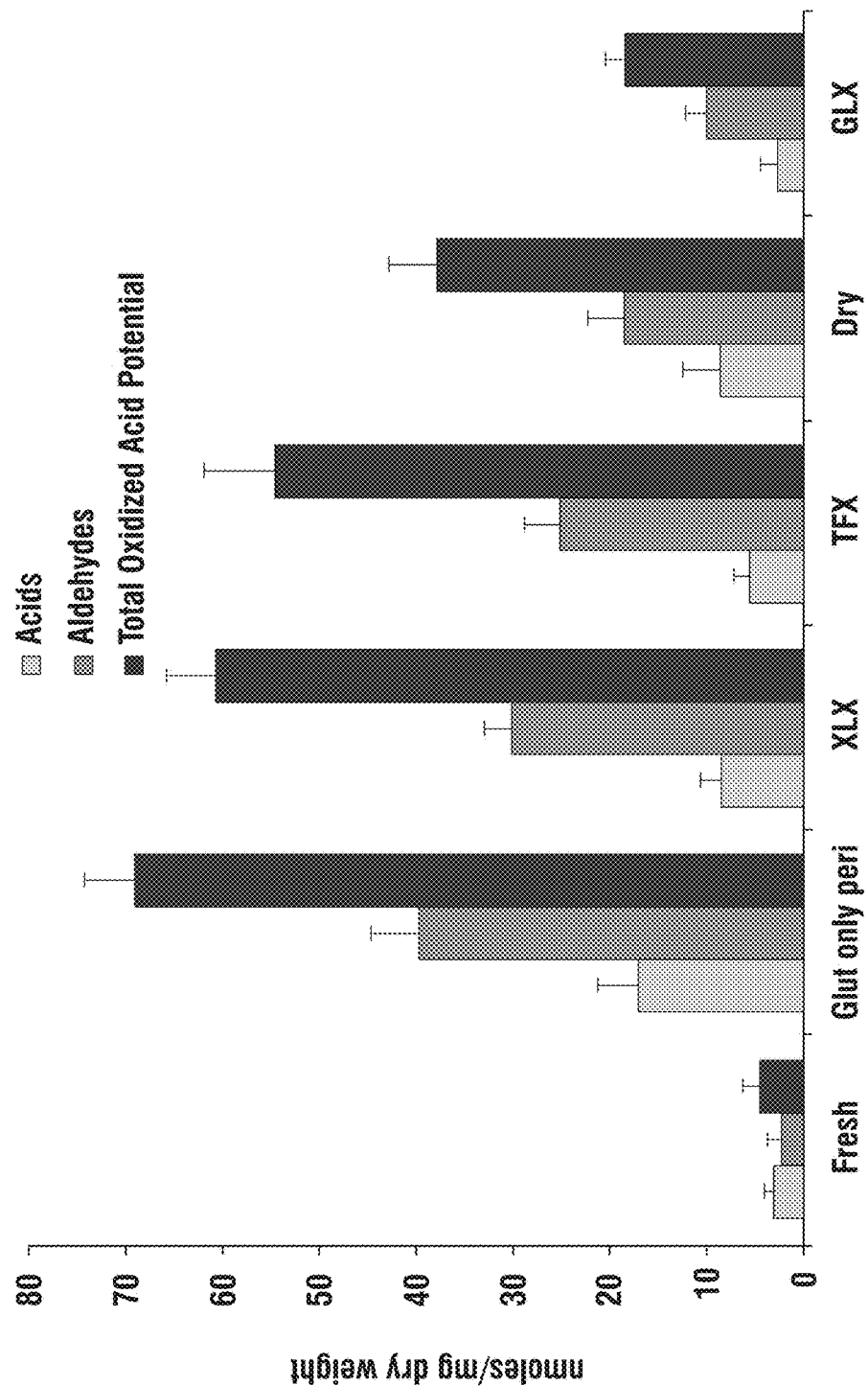
FIG. 3 is a graph illustrating the acid and aldehyde content of various tissue treatments.

As mentioned above, it is now understood that oxidation of the aldehyde groups in tissue to carboxylic acid groups produces an increase in calcification. Evidence of this phenomenon is provided in the graph of FIG. 3. Specifically, as explained above, the level of acids in the tissue correlates directly with the propensity to calcify after implant. FIG. 3 indicates the acid levels in various tissue samples. The types of tissue treatments are fresh untreated tissue, glutaraldehyde-fixed tissue, XenoLogiX (XLX), ThermaFix (TFX), ThermaFix tissue treated with glycerol and ethanol only, and the GLX process, which includes treatment with glutaraldehyde, capped with ethanolamine while being reduced with sodium borohydride, and dehydrated with glycerol and ethanol.

Figure 4:
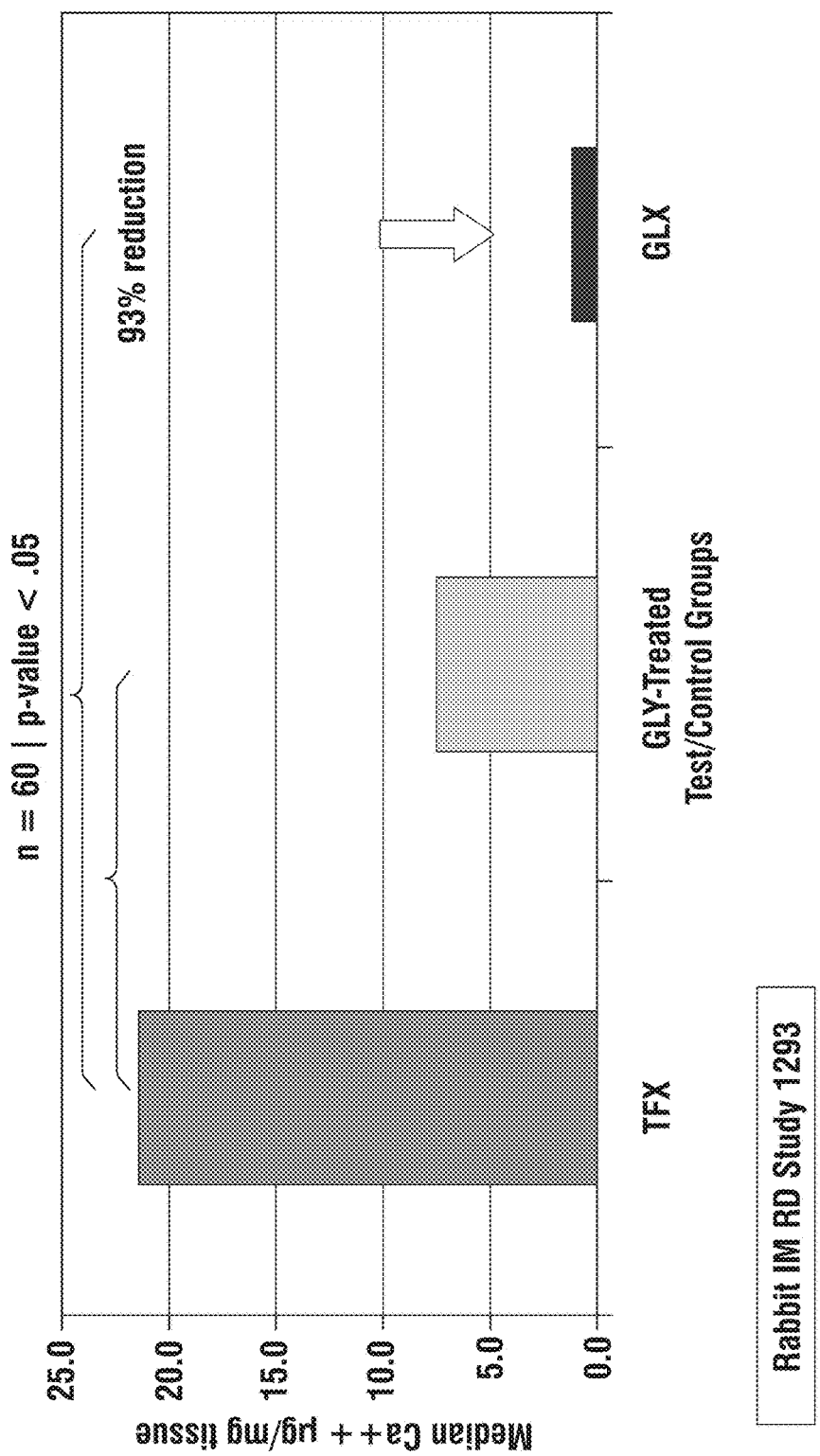
FIG. 4 is a chart showing the decrease in calcification by capping, reduction and drying (GLX process)

FIGS. 4 and 5 are the results of a rabbit intramuscular implant study indicating that the GLX process (described in this invention) significantly reduces calcification over current technology (TFX) and over simple glycerol treatment (GLY-treated). These data also indicate that the GLX process reduces variability in calcification. All calcification measurements were measured by atomic absorption spectroscopy and normalized to dry weight of lyophilized tissue.

FIGS. 6 and 7 illustrate that after 80 days of real time shelf life, the GLX treated tissue shows significantly less calcification than TFX or the glycerol treatment alone. The GLX process also reduces variability after 80 days of shelf life. All calcification measurements were measured by atomic absorption spectroscopy and normalized to dry weight of lyophilized tissue.

Based on the foregoing empirical results, the inventors believe that the oxidative damage of dehydrated tissue imparted on bioprosthetic tissue greatly contributes to the propensity for calcification of tissue. In particular, heart valve leaflets not stored in glutaraldehyde are subjected to significant oxidative damage. This deleterious tissue damage process can create new binding sites not previously detected or recognized, as potential attachment sites of calcium and phosphate ions, thereby initiating calcification.

To help prevent this post-implant damage-calcification process, the present invention involves mitigating oxidation by capping the numerous aldehydes that are susceptible to oxidation and increased calcification initiation.

The preferred embodiments include, but are not limited to:

1. The fixed tissue valve or tissue sheet is treated in a solution containing an aldehyde capping agent.
2. Embodiment 1, but where a sterilization step is added during or after the capping process.
3. Embodiments 1 and 2, but where the processing is agitated.
4. Embodiments 1, 2, and 3, but where the capping agent is for the other binding sites such as acids or biological-immune related sites.
5. The aldehyde capping solution may contain an amine (10 mM ethanolamine) and a reducing agent (132 mM sodium borohydride) in 50 mM phosphate buffer at pH 7.4.
6. The tissue or valve is then dehydrated in a glycerol solution
7. The tissue or valve is then sterilized with ethylene oxide Example 1

Aldehyde capping using ethanolamine and sodium borohydride of glutaraldehyde-fixed tissue. Bioprosthetic tissue was removed from 0.625% glutaraldehyde just after heat treatment step and rinsed in ethanol:saline (20%/80%) for 2 minutes. One liter of capping solution was prepared containing 10 mM ethanolamine (0.06%), and 110 mM sodium borohydride (0.42%) in 50 mM phosphate buffer (pH 7.3-7.8)

The capping solution was placed on an orbital shaker, then tissues (leaflets or valves) were placed in the solution so that they were completely submerged. The ratio of tissue to solution was 3 leaflets per 100 ml or one valve per 100 ml. The container was partly covered but not completely sealed because hydrogen gas liberated by the chemical reaction with water could cause the container to explode. The orbital shaker was operated at between 80-100 rpm for 4 hours at room temperature. The tissue was removed and rinsed in FET solution (formaldehyde, ethanol, tween-80) for three minutes.

Example 2

Glycerol dehydration process for pericardial valve bioprosthesis. Pericardial valves were dehydrated by holding each valve with forceps on the sewing ring of the valve and placing the valve in a glycerol/ethanol (75%/25%) mixture. Beakers containing the valves were placed on an orbital shaker operating between 50-60 RPM for at least one (1) hour but not more than four (4) hours then immediately treated to remove excess glycerol. This was done by holding them with forceps on the sewing ring of the valve, taking the valve out of the glycerol/ethanol mixture and then placing it on an absorbent towel in a wide mouth jar. After being allowed to dry for at least 5 minutes at room temperature the jar was attached to a lyophilizer and dried for 2 hours. Valves were then transferred to ethylene oxide gas permeable packages and sterilized with ethylene oxide.

Example 3

Calcification Mitigation—Small Animal Model. In order to evaluate the calcification mitigation properties of GLX treated and EO sterilized pericardial tissue, two small animal feasibility studies were conducted. These studies demonstrate that, 1) GLX is superior to TFX in mitigating the occurrence of calcification in tissue, and 2) real time aged GLX tissue is also superior to TFX in mitigating calcification. In both studies, GLX valves demonstrated reduced variability in calcification data when compared to TFX valves. Test methods and results of each are summarized below.

Example 3A

Rabbit Study #1. Calcification Potential of Ethylene Oxide Sterilization on GLX Processed Pericardial Tissue in a 35 Day Rabbit Intramuscular Study. A study utilizing sixty (60) rabbits was conducted to look at the effects on calcification of GLX treated pericardium sterilized using 100% ethylene oxide. The control group was ThermaFix (TFX) processed bovine pericardium and the test group was GLX processed pericardium. Using a sign-rank test, GLX tissue was found to be significantly different (p=0.0004) when compared to TFX, and demonstrated a 93% calcification reduction over TFX. GLX data also showed reduced outliers and reduced variability. Box and Whisker plots show an appreciable reduction in variability with the GLX process. Data are presented in FIG. 7, with the y-axis measuring μg calcium/mg dry weight tissue.

Example 3B

Rabbit Study #2. Effects of a Short Term Shelf Life on Calcification of GLX Processed Pericardial Tissue in a 35 Day Rabbit Intramuscular Study. A second study utilizing sixty (60) additional rabbits was conducted to look at the effects on calcification of short term shelf life of GLX processed pericardium. The control group was ThermaFix (TFX) processed bovine pericardium and the test group was GLX processed pericardium. The GLX tissue samples were packaged in Tyvek pouches and sterilized via 100% ethylene oxide. GLX samples were stored in a controlled steady state chamber at 25° C. and 60% humidity for a period of 83 days. The TFX samples had not been aged. In this study the GLX processed tissue demonstrated significantly reduced levels of calcification, 73% compared (p=0.009) to TFX as well as reduced outliers and reduced variability in the data. Data are presented in FIG. 8, with the y-axis measuring μg calcium/mg dry weight tissue.

While the invention has been described in its preferred embodiments, it is to be understood that the words which have been used are words of description and not of limitation. Therefore, changes may be made within the appended claims without departing from the true scope of the invention.

What is claimed is:

1. A packaged bioprosthetic device comprising:
   an at least partially cross-linked pericardial tissue comprising functional groups that have been blocked, removed or altered by reacting the functional groups with capping agents, wherein the functional groups are one or both of aldehyde groups and carboxylic acid groups; and
   a packaging storing the at least partially cross-linked biological tissue without a liquid preservative solution.

2. The packaged bioprosthetic device of claim 1, wherein the bioprosthetic device is a bioprosthetic heart valve comprising a stent coupled to leaflets made from the at least partially cross-linked biological tissue.

3. The packaged bioprosthetic device of claim 1, wherein the biological tissue is at least partially cross-linked with glutaraldehyde or other aldehyde-containing agents.

4. The packaged bioprosthetic device of claim 1, wherein the at least a portion of the functional groups are blocked, removed or altered by exposing the at least partially cross-linked biological tissue to a reducing agent.

5. The packaged bioprosthetic device of claim 1, wherein the at least partially cross-linked biological tissue comprises glycerol.

6. The packaged bioprosthetic device of claim 5, wherein the at least partially cross-linked biological tissue and the packaging is sterilized by ethylene oxide, gamma irradiation or electron beam irradiation.

7. The packaged bioprosthetic device of claim 1, wherein the at least partially cross-linked biological tissue is at least partially dehydrated.

8. The packaged bioprosthetic device of claim 7, wherein the at least partially cross-linked biological tissue and the packaging is sterilized by ethylene oxide, gamma irradiation or electron beam irradiation.

9. The packaged bioprosthetic device of claim 1, wherein the capping agent is one or more selected from the group consisting of: an amine, an alkyl amine, an amino alcohol, an ethanolamine, an amino acid, a lysine, a hydroxylysine, an amino sulfonate, a taurine, an amino sulfate, a dextran sulfate, a chondroitin sulfate, a hydrophilic multifunctional polymer, a polyvinyl alcohol, a polyethyleneimine, a hydrophobic multifunctional polymer, an α-dicarbonyl, a methylglyoxal, a 3-deoxyglucose, a glyoxal, a hydrazide, an adipic hydrazide, a heparin, a mono-epoxy alkane, a di-epoxy alkane, and a polyepoxyalkane.

10. The packaged bioprosthetic device of claim 9, wherein the functional groups have been reacted with a reducing agent.

11. The packaged bioprosthetic device of claim 10, wherein the reducing agent is selected from the group consisting of: a sodium borohydride and a sodium cyanoborohydride.

12. The packaged bioprosthetic device of claim 11, wherein the bioprosthetic tissue comprises glycerol.

13. The packaged bioprosthetic device of claim 1, wherein the biological tissue is at least partially cross-linked with glutaraldehyde or an aldehyde-containing agent.

14. The packaged bioprosthetic device of claim 1, wherein the capping agent is one or more selected from the group consisting of: an amine, an alkyl amine, an amino alcohol, an ethanolamine, an amino acid, a lysine, a hydroxylysine, an amino sulfonate, a taurine, an amino sulfate, a dextran sulfate, a chondroitin sulfate, a hydrophilic multifunctional polymer, a polyvinyl alcohol, a polyethyleneimine, a hydrophobic multifunctional polymer, an α-dicarbonyl, a methylglyoxal, a 3-deoxyglucose, a glyoxal, a hydrazide, an adipic hydrazide, a heparin, a mono-epoxy alkane, a di-epoxy alkane, and a polyepoxyalkane.

15. The packaged bioprosthetic device of claim 1, wherein the functional groups have been reacted with a reducing agent.

16. The packaged bioprosthetic device of claim 15, wherein the reducing agent is selected from the group consisting of: a sodium borohydride and a sodium cyanoborohydride.

17. The packaged bioprosthetic device of claim 16, wherein the bioprosthetic tissue comprises glycerol.

\* \* \* \* \*